United States Patent
Thomas et al.

(10) Patent No.: US 11,726,053 B2
(45) Date of Patent: Aug. 15, 2023

(54) SYSTEMS AND METHODS FOR ELECTRICAL MEASUREMENTS OF A PLANT STALK

(71) Applicant: Brigham Young University (BYU), Provo, UT (US)

(72) Inventors: Mavrik D. Thomas, Overland Park, KS (US); Douglas D. Cook, Fountain Green, UT (US); Brian Anthony Mazzeo, Provo, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 17/657,240

(22) Filed: Mar. 30, 2022

(65) Prior Publication Data
US 2022/0317079 A1     Oct. 6, 2022

Related U.S. Application Data

(60) Provisional application No. 63/200,813, filed on Mar. 30, 2021.

(51) Int. Cl.
*G01N 27/24*     (2006.01)
*G01N 33/00*     (2006.01)
*G01N 27/22*     (2006.01)

(52) U.S. Cl.
CPC .......... *G01N 27/24* (2013.01); *G01N 27/226* (2013.01); *G01N 33/0098* (2013.01)

(58) Field of Classification Search
CPC . G01N 33/0098; G01N 27/221; G01N 27/226
See application file for complete search history.

(56) References Cited

U.S. PATENT DOCUMENTS

| | | | |
|---|---|---|---|
| 2015/0027044 A1* | 1/2015 | Redden | A01M 21/043 |
| | | | 47/58.1 R |
| 2019/0195762 A1* | 6/2019 | Brune | A01B 79/005 |
| 2019/0335684 A1* | 11/2019 | Redden | A01M 21/043 |

FOREIGN PATENT DOCUMENTS

WO     WO-9938370 A1 *    8/1999    ............... A01G 3/00

* cited by examiner

*Primary Examiner* — Alvaro E Fortich
(74) *Attorney, Agent, or Firm* — Brake Hughes Bellermann LLP

(57) ABSTRACT

An apparatus configured to perform non-destructive, electrical measurements on a plant stalk to detect and quantify internal damage is disclosed. This apparatus includes features to minimize misalignments that can negatively affect the precision and/or accuracy of the electrical measurements.

19 Claims, 13 Drawing Sheets

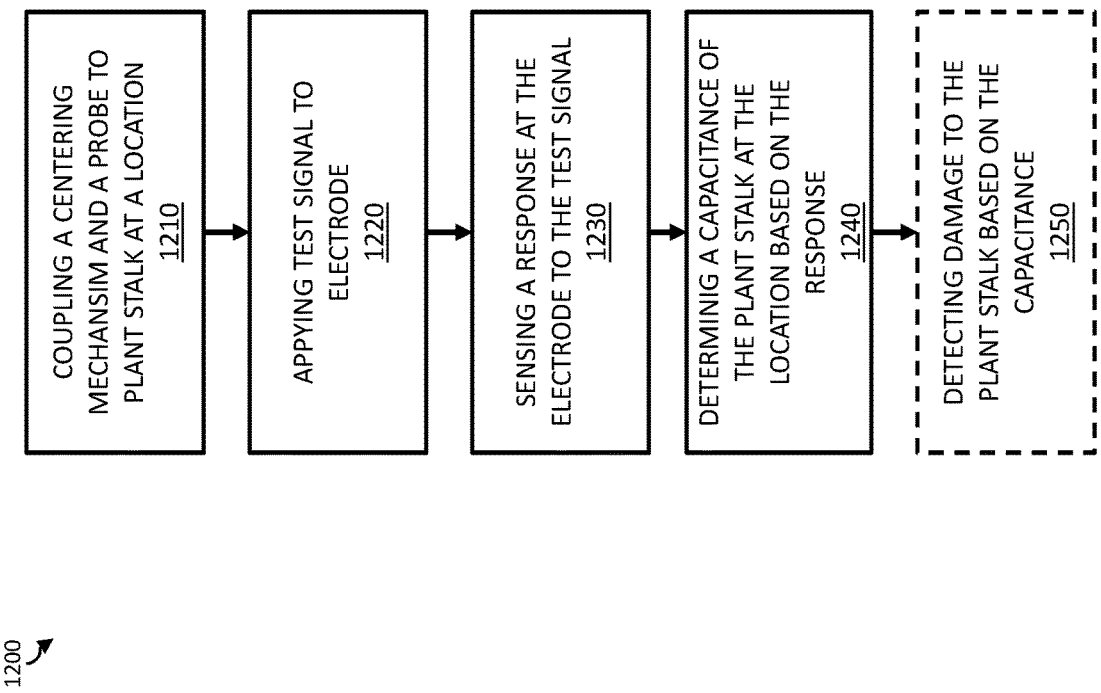

SYSTEMS AND METHODS FOR ELECTRICAL MEASUREMENTS OF A PLANT STALK

CROSS-REFERENCE TO RELATED APPLICATION

This application claims the benefit of U.S. Provisional Application No. 62/200,813, filed on Mar. 30, 2021, which is hereby incorporated by reference in its entirety.

FIELD OF THE DISCLOSURE

The present disclosure relates to electrical measurements of plant material and more specifically to an apparatus for positioning and measuring a plant stalk for interior damage.

BACKGROUND

The European Corn Borer (ECB), *Ostrinia nubilalis*, is an agricultural pest which bores small holes in the rind of maize stalks and then proceeds to consume the pith. Because most of the damage to the stalk is internal, it is difficult to quantify the damage to an individual stalk without time-consuming, manual examination.

SUMMARY

In some aspects, the techniques described herein relate to an apparatus, including: a centering mechanism configured to be coupled to a plant stalk; a probe movably coupled to the centering mechanism and having an electrode; and a first biasing mechanism configured to maintain contact of the electrode with a portion of the plant stalk while the centering mechanism is coupled to the plant stalk and during a measurement cycle using the electrode.

In some aspects, the techniques described herein relate to an apparatus, wherein the centering mechanism includes: a first arm including a first centering feature configured to receive the plant stalk; a second arm including a second centering feature to receive the plant stalk; and a clamping mechanism configured to press the plant stalk between the first arm and the second arm so that the plant stalk is held by the first centering feature and the second centering feature.

In some aspects, the techniques described herein relate to an apparatus, wherein the first centering feature and the second centering feature reduce an offset between the plant stalk and the electrode when the plant stalk is held by the first centering feature and the second centering feature.

In some aspects, the techniques described herein relate to an apparatus, wherein: the first centering feature is a first V-shape having a first opening facing a surface of the plant stalk; and the second centering feature is a second V-shape having a second opening facing the surface of the plant stalk.

In some aspects, the techniques described herein relate to an apparatus, wherein: the first arm is fixed with respect to the second arm; and the second arm is movable with respect to the first arm.

In some aspects, the techniques described herein relate to an apparatus, wherein the electrode is a guarded electrode, and the probe further includes a counter electrode, the guarded electrode and the counter electrode.

In some aspects, the techniques described herein relate to an apparatus, wherein the guarded electrode and the counter electrode are configured to contact opposite sides of the plant stalk, respectively, during the measurement cycle.

In some aspects, the techniques described herein relate to an apparatus, wherein the guarded electrode and the counter electrode each contact a side of the plant stalk during the measurement cycle.

In some aspects, the techniques described herein relate to an apparatus, wherein the probe further includes a guard ring, the guard ring surrounding the guarded electrode in a plane of the guarded electrode.

In some aspects, the techniques described herein relate to an apparatus, wherein the probe includes a plunger having a rod portion movable in an opening of the centering mechanism and a plate portion configured to support the electrode.

In some aspects, the techniques described herein relate to an apparatus, wherein the first biasing mechanism is a spring positioned along the rod portion and configured to press the electrode on the plate portion against the portion of the plant stalk.

In some aspects, the techniques described herein relate to a method for detecting damage to a plant stalk, including: coupling a centering mechanism and a probe to the plant stalk at a location, the probe movably coupled to the centering mechanism via a biasing mechanism and having an electrode such that the biasing mechanism maintains contact of the electrode with the plant stalk; applying a test signal to the electrode; sensing a response, at the electrode, to the test signal; and determining a capacitance of the plant stalk at the location based on the response.

In some aspects, the techniques described herein relate to a method for detecting damage to the plant stalk, wherein the probe is a first probe, the biasing mechanism is a first biasing mechanism, the electrode is a first electrode, the coupling including: coupling a first arm of the centering mechanism to a first side of the plant stalk, the first arm coupled to the first probe via the first biasing mechanism; and coupling a second arm of the centering mechanism to a second side of the plant stalk, the second arm coupled to a second probe via a second biasing mechanism, the second probe including a second electrode.

In some aspects, the techniques described herein relate to a method for detecting damage to a plant stalk, wherein the coupling further includes: positioning the plant stalk between the first arm and the second arm when the first arm and the second arm define an open configuration; and clamping the first arm and the second arm around the plant stalk, in a closed configuration, to align the plant stalk and reduce an offset between the plant stalk and the first electrode and the second electrode, the first biasing mechanism pressing the first electrode against a surface of the plant stalk and the second biasing mechanism pressing the second electrode against the surface of the plant stalk to reduce a gap between the plant stalk and the first electrode and the second electrode.

In some aspects, the techniques described herein relate to a method for detecting damage to the plant stalk, wherein sensing of the response of the first electrode to the test signal includes: measuring the capacitance between the first electrode and the second electrode as the capacitance of the plant stalk at the location.

In some aspects, the techniques described herein relate to a method for detecting damage to the plant stalk, wherein the test signal is an alternating current (AC) voltage that is swept through a range of frequencies.

In some aspects, the techniques described herein relate to a method for detecting damage to the plant stalk, wherein sensing of the response of the electrode to the test signal includes measuring an amplitude and phase of a voltage across a reference resistor that is coupled in series with the electrode.

In some aspects, the techniques described herein relate to a method for detecting damage to the plant stalk, wherein the test signal is digital signal that is transition from a LOW level to a HIGH level.

In some aspects, the techniques described herein relate to a method for detecting damage to the plant stalk, wherein sensing the response of the electrode to the test signal includes measuring an RC time constant of a voltage across a reference resistor that is coupled in series with the electrode.

In some aspects, the techniques described herein relate to a method for detecting damage to the plant stalk, wherein the location is a first location, the test signal is a first test signal, the method further including: decoupling the probe from the plant stalk at the first location; coupling the probe to the plant stalk at a second location; applying a second test signal to the electrode; sensing a response to the second test signal using the electrode; determining a capacitance of the plant stalk at the second location based on the response to the second test signal; and comparing the capacitance of the plant stalk at the first location and the capacitance of the plant stalk at the second location to detect damage to the plant stalk.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

FIG. 12 is a flowchart of a method for detecting damage to a plant stalk according to an implementation of the present disclosure.

The components in the drawings are not necessarily to scale relative to each other. Like reference numerals designate corresponding parts throughout the several views.

DETAILED DESCRIPTION

One challenge to growing maize in Europe and North America is the European Corn Borer, *Ostrinia nubilalis* (ECB), which can bore holes in the surface rind of maize stalks and consume the interior pith. ECB damage primarily occurs inside of corn stalks and is rarely visible from the outside. Detecting and quantifying internal damage can be destructive to the plant and can require significant manual labor.

The present disclosure describes an apparatus configured to perform non-destructive, electrical measurements on a plant stalk to detect and quantify internal damage (e.g., voids). This approach can save time and labor in testing for internal plant damage caused by a pest (e.g., ECB) and may improve the quantification of an infestation to help assess the impact of a pest management.

An electrical measurement can determine a relative permittivity of the plant stalk to detect and quantify internal damage. For example, an area of a plant stalk that is intact may have a higher relative permittivity than an area of the plant stalk that is damaged (e.g., has an internal void). The disclosed apparatus can be configured to measure a capacitance to determine the relative permittivity of a plant stalk in a test area.

Figure 1:
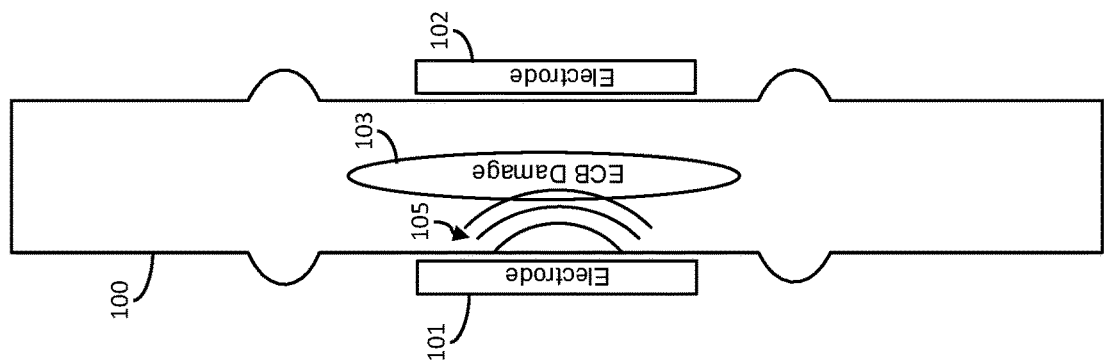
FIG. 1 is a side view of an electrical measurement to detect an interior damage to a plant stalk according to possible implementations of the present disclosure.

FIG. 1 is a side view of an electrical (e.g., capacitance) measurement to detect an interior damage to a plant stalk according to a possible implementation of the present disclosure. In the measurement, a plant stalk 100 (e.g., maize stalk) may be positioned within fields 105 created by two electrodes. For example, as shown in FIG. 1, the plant stalk may be positioned between a first electrode 101 and a second electrode 102. The ratio of an electric charge accumulation on the electrodes to an applied electric potential between the two electrodes is a capacitance. The capacitance may depend on (at least) the separation between the electrodes, the surface area of the electrodes, and the permittivity of the plant stalk 100 between the electrodes. Interior damage (i.e., damage 103) to the plant stalk 100 can be characterized by a change in the amount of material within the stalk. For example, ECB damage due to larvae tunneling can result in a replacement of the pith material with air and frass (i.e., larval excrement). In other words, damage to the plant stalk may correspond with a hollow area (i.e., void) in the plant stalk. This damage can decrease a measurable relative permittivity in the area of the damage 103.

Testing for damage 103 to a plant stalk 100 may include positioning the first electrode 101 and the second electrode 102 at a location along a length of the plant stalk. The testing may further include applying an electric field to measure a capacitance of a capacitor formed by the first electrode 101, the second electrode 102, and the portion of the plant stalk in an electric field created by the electrodes. In a possible implementation, the capacitance measurement may include combining (e.g., averaging) multiple capacitance measurements at the location to generate a representative capacitance measurement corresponding to the location. The testing may further include performing capacitance measurements at a plurality of locations along a length of the plant stalk.

The testing may further include comparing capacitance measurements from different locations to detect a difference. In a possible implementation, the testing may include comparing the difference to a threshold to determine a binary damage status (i.e., damage/no-damage) of the plant stalk. For example, a difference between a maximum capacitance measurement of a plant stalk and a minimum capacitance measurement of the plant stalk that is above a threshold may indicate that the plant stalk is damaged. The threshold may be based on a training phase including measuring and correlating capacitances and damage using samples with known damage.

The testing may further include determining that a location of the plurality locations includes damage based on the capacitance measurements from the plurality of locations. For example, the testing may include determining a statistical difference (e.g., difference from a mean capacitance) in the capacitance measurement from a location with damage. For example, a measured capacitance at a location that is lower than the threshold may indicate damage at the location. In a possible implementation, the threshold may correspond to measurements taken at the plurality of locations along the length of the plant stalk. For example, the threshold may correspond to an average capacitance of the locations. A plant stalk may include multiple locations having a measured capacitance that is below the threshold (i.e., multiple locations may have damage). The testing may be able to identify each of the locations.

The testing may further include estimating an amount (e.g., percentage) of damage based on a magnitude of the difference. For example, a difference (e.g., decrease) between the highest capacitance measured and the capacitance at a location may correspond to an amount (e.g., percentage) of damage at the location.

A precision and an accuracy of the testing may be affected by relative positions of one or more of the electrodes and the plant stalk. Accordingly, the disclosed electrical measurement apparatus for a plant stalk includes features to control the relative positioning during a measurement cycle, where the measurement cycle includes one or more capacitance measurements.

Figure 2:
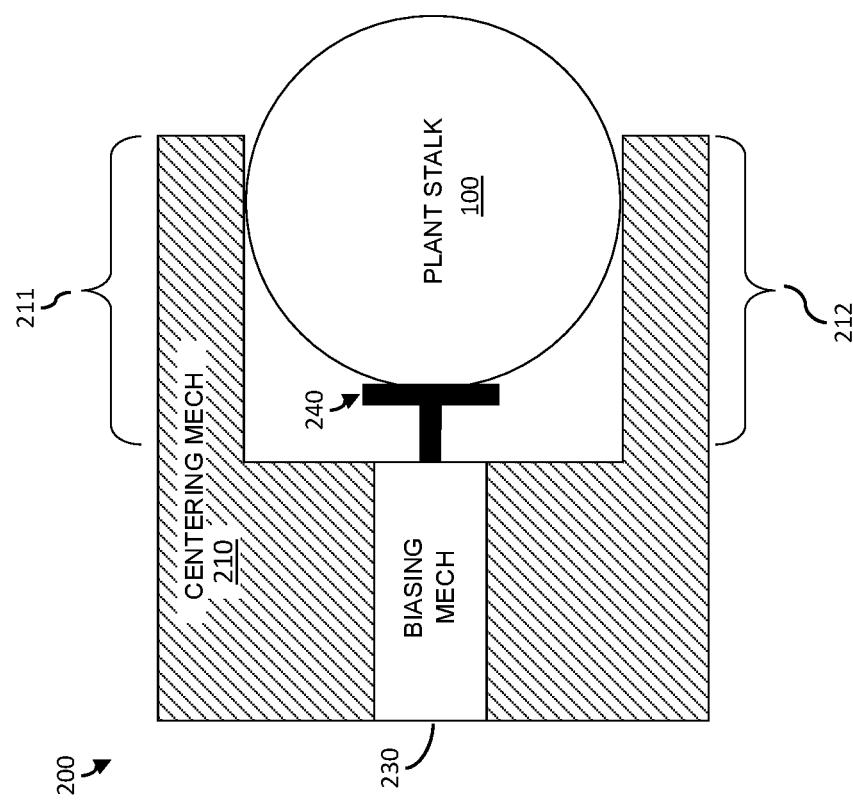
FIG. 2 is a block diagram of an electrical measurement apparatus for a plant stalk according to a possible implementation of the present disclosure.

FIG. 2 is a block diagram of an electrical measurement apparatus for a plant stalk according to a possible implementation of the present disclosure. As shown, the apparatus includes a centering mechanism 210. The centering mechanism 210 is configured to be mechanically coupled to the plant stalk. For example, the plant stalk may be received by an opening formed by a first arm portion (i.e., first arm 211) and a second arm portion (i.e., second arm 212). The opening may be sized to match a diameter of the plant stalk 100. For example, the first arm portion 211 and the second arm portion may grip a surface of the plant stalk to hold in in a position that is centered with respected to a probe 240. The probe may be movably coupled to the centering mechanism 210 so that an electrode on the probe 240 may be moved to contact a surface of the plant stalk 100. As shown, the apparatus 200 further includes a biasing mechanism. The biasing mechanism can be configured to push the electrode of the probe against a surface of the plant stalk while the centering mechanism is coupled to the plant stalk. The electrode may then be used in a capacitance measurement cycle (i.e., measurement cycle). The centering function of the centering mechanism 210 and the mechanical biasing function of the biasing mechanism can help to minimize variations in alignment that could cause variations in capacitance measurements of the plant stalk.

In a possible implementation, the first arm portion (i.e., first arm 211) and the second arm portion (i.e., second arm 212) include a shape capable of receiving and positioning plant stalks having a range of possible diameters. The shape may be further capable of receiving and positioning plant stalks that are approximately circular, (e.g., oval).

In a possible implementation, the first arm 211 and the second arm 212 can be moved to clamp the plant stalk. For example, a clamping mechanism may press the first arm 211 and the second arm 212 against the surface of the plant stalk on different sides (e.g., at diametrically opposite positions). In a possible implementation, only one of the arms is movable while the other is fixed relative to the moving arm. For example, the first arm can be fixed with respect to the movable second arm. The clamping mechanism may press the movable second arm towards the fixed first arm to clamp the plant stalk between the arms. The pressing force provided by the clamping mechanism may result from a variety of possible mechanical energy sources such as a spring, elastic body, screw, wedge, or the like.

Figure 3A:
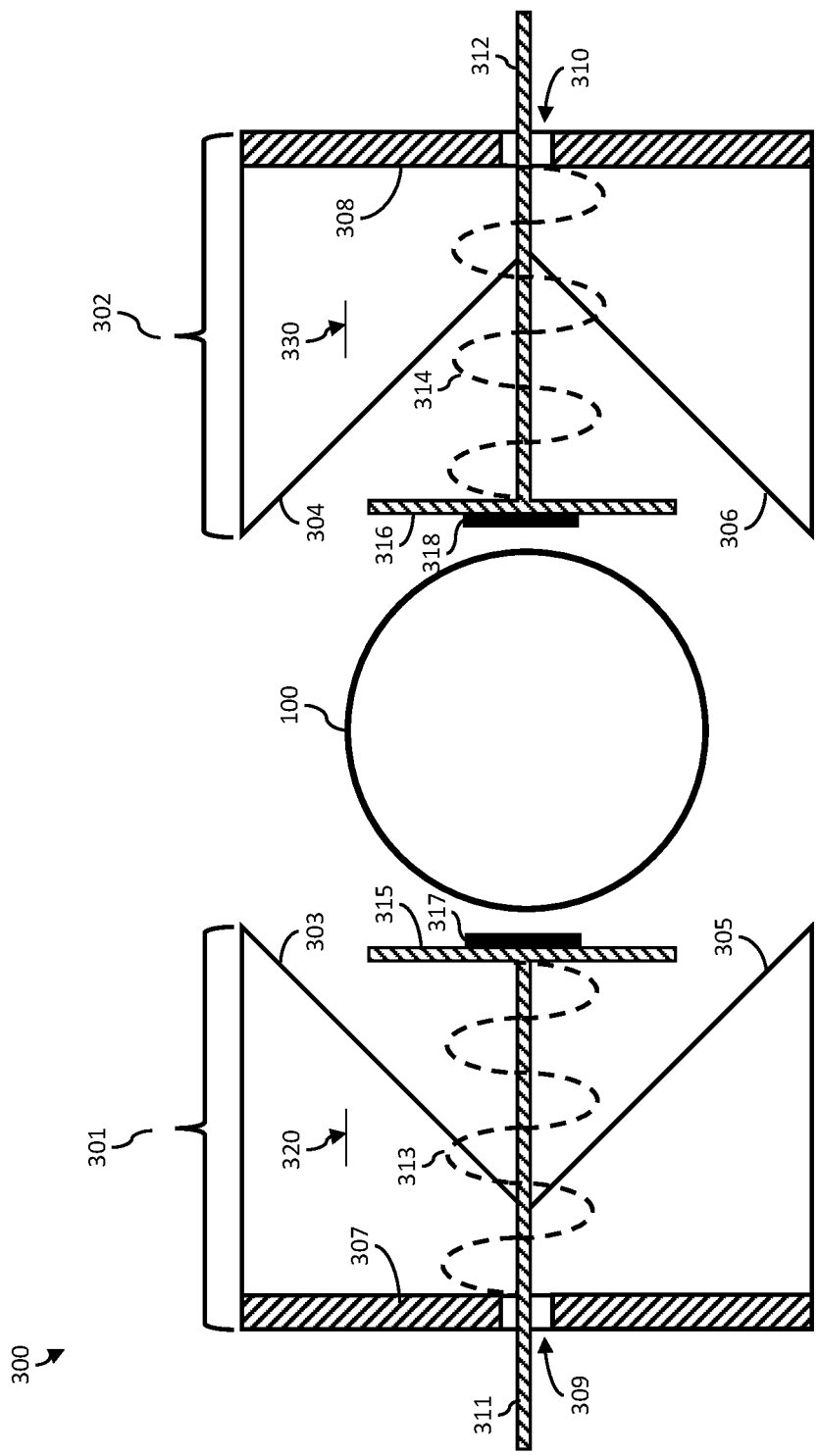
FIG. 3A is a top view of a possible implementation of the electrical measurement apparatus in an open configuration according to possible implementations of the present disclosure.

FIG. 3A illustrates a possible implementation of the electrical measurement apparatus from a top view. As shown, the electrical measurement apparatus (i.e., apparatus 300) is in an open configuration. In the open configuration, a first arm 301 and a second arm 302 are spaced apart so that the plant stalk 100 is not coupled by the arms. Additionally, in the open configuration, a first electrode 317 of a first probe and a second electrode 318 of a second probe are spaced apart so that they are not in contact with a surface of the plant stalk 100. In the open configuration, a user may position the plant stalk between a first arm 301 (and first electrode 317) and a second arm 302 (and second electrode 318) and position the apparatus at to a location along a length of the stalk.

As mentioned, the apparatus 300 includes a first arm 301 and a second arm 302. The first arm 301 and the second arm 302 can be position at opposite sides of the plant stalk 100. For example, the arms may be coupled to a rail (not shown) allowing one, or both, arms to move together or apart along the rail. When both arms are moved, the movement of the arms may be simultaneous.

The first arm 301 includes a first base portion 307 and a first clamping portion 320. The first clamping portion 320 includes a centering feature. The centering feature (i.e., centering profile, centering surface) includes a first ramp surface 303 and a second ramp surface 305 that intersect at a vertex of a V-shaped opening. When the first arm 301 is moved toward a plant stalk 100 (or the plant stalk is moved toward the first arm 301), the plant stalk is guided by the first ramp surface 303 and the second ramp surface 305 to a centered position relative to the first arm 301. In the centered position relative to the first arm 301, a center of the plant stalk may be substantially aligned (e.g., in line with) with the vertex of the V-shaped opening.

In some implementations, the first ramp surface 303, the second ramp surface 304, the third ramp surface 305, and the fourth ramp surface 305 can be collectively referred to as ramp surfaces. One or more of the ramp surfaces can be referred to as tapered surfaces. In some implementations, the shape of one or more of the ramp surfaces can be different than shown in FIG. 3A. For example, in some implementations, one or more of the ramp surfaces can have a curved shape (e.g., arc shape). In some implementations, one or more of the ramp surfaces can have one or more protrusions, or sharp edges that can be used to engage a surface.

The second arm 302 includes a second base portion 308 and a second clamping portion 330. The second clamping portion 330 includes a centering feature. The centering feature includes a first ramp surface 304 and a second ramp surface 306 that intersect at a vertex of a V-shaped opening. The V-shaped opening of the second arm 302 is opposite (i.e., faces) the V-shaped opening of the first arm 301. When the second arm 302 is moved toward the plant stalk 100 (or the plant stalk is moved toward the second arm 302), the plant stalk is guided by the first ramp surface 304 and the second ramp surface 306 to a centered position relative to the second arm 302. In the centered position relative to the second arm 302, a center of the plant stalk may be substantially aligned (e.g., in line with) with the vertex of the V-shaped opening.

It should be noted that in a possible implementation, the first arm 301 may include multiple clamping portions for added clamping strength/stability. The multiple clamping portions of the first arm 301 may be coupled to the first base portion 307 so that their respective centering features engage with different locations along a length of the plant stalk. Additionally, or alternatively, the second arm 302 may include multiple clamping portions. The multiple clamping portions of the second arm 30 may be coupled to the second base portion 308 so that their respective centering features engage with different locations along the length of the plant stalk. In a possible implementation, the locations engaged by the multiple centering features of the first arm 301 may alternate along the length of the plant stalk with the locations engaged by the multiple centering features of the second arm 302.

The first base portion 307 of the first arm 301 can include an opening 309 configured to receive a first rod portion 311 of a first probe so that the first probe may remain in a fixed position (e.g., against a first side of the plant stalk) as the first arm 301 is moved (e.g., towards the first side). In a possible implementation the opening 309 may be sized/shaped to guide the first rod portion 311 of the first probe so that the first electrode 317 remains in proper alignment (e.g., tangential) with a surface of the plant stalk 100.

Likewise, the second base portion 308 of the second arm 302 can include an opening 310 configured to receive a rod portion 312 of a second probe so that the second probe may remain in a fixed position (e.g., against a second side of the plant stalk) as the second arm 302 is moved (e.g., towards the second side). In a possible implementation, the opening 310 may be sized/shaped to guide the second rod portion 312 of the probe so that the second electrode 318 remains in proper alignment (e.g., tangential) with the surface of the plant stalk 100.

A first probe of the apparatus 300 may include a first rod portion 311 coupled to a first plate portion 315. In a possible implementation the first rod portion 311 and the first plate portion 315 are portions of a unitary body. The first probe further includes a first electrode 317. The first plate portion 315 is configured to mechanically support and position the first electrode 317. Accordingly, the first plate portion 315 may have a size and a shape corresponding to the physical dimensions of the first electrode 317.

As shown, the apparatus 300 may further include a second probe. The second probe of the apparatus 300 may include a second rod portion 312 coupled to a second plate portion 316. In a possible implementation the second rod portion 312 and the second plate portion 316 are portions of a unitary body. The second probe further includes a second electrode 318. The second plate portion 316 is configured to mechanically support and position the second electrode 318. Accordingly, the second plate portion 316 may have a size and a shape corresponding to the physical dimensions of the second electrode 318.

In possible implementation, the first arm 301 may be moved so that the plant stalk 100 is in contact with the first ramp surface 303 and the second ramp surface 305 of the first clamping portion 320. In a possible implementation, the second arm 302 may be moved so that the plant stalk 100 is in contact with the first ramp surface 304 and the second ramp surface 306 of the second clamping portion 330. In other words, the apparatus 300 may be configured into a closed configuration (i.e., clamping configuration, centering configuration) in which the plant stalk 100 is held (i.e., griped, clamped) by the first centering feature of the first arm 301 and the second centering feature of the second arm 302.

A clamping mechanism (not shown) may produce a first clamping force 341 and a second clamping force 342. The first clamping force 341 and the second clamping force 342 can press the plant stalk 100 between the first arm 301 and the second arm 302. For example, the clamping mechanism may include a spring (not shown) with a force that pulls the first arm 301 and the second arm 302 together along rails (not shown towards the plant stalk 100.

Figure 3B:
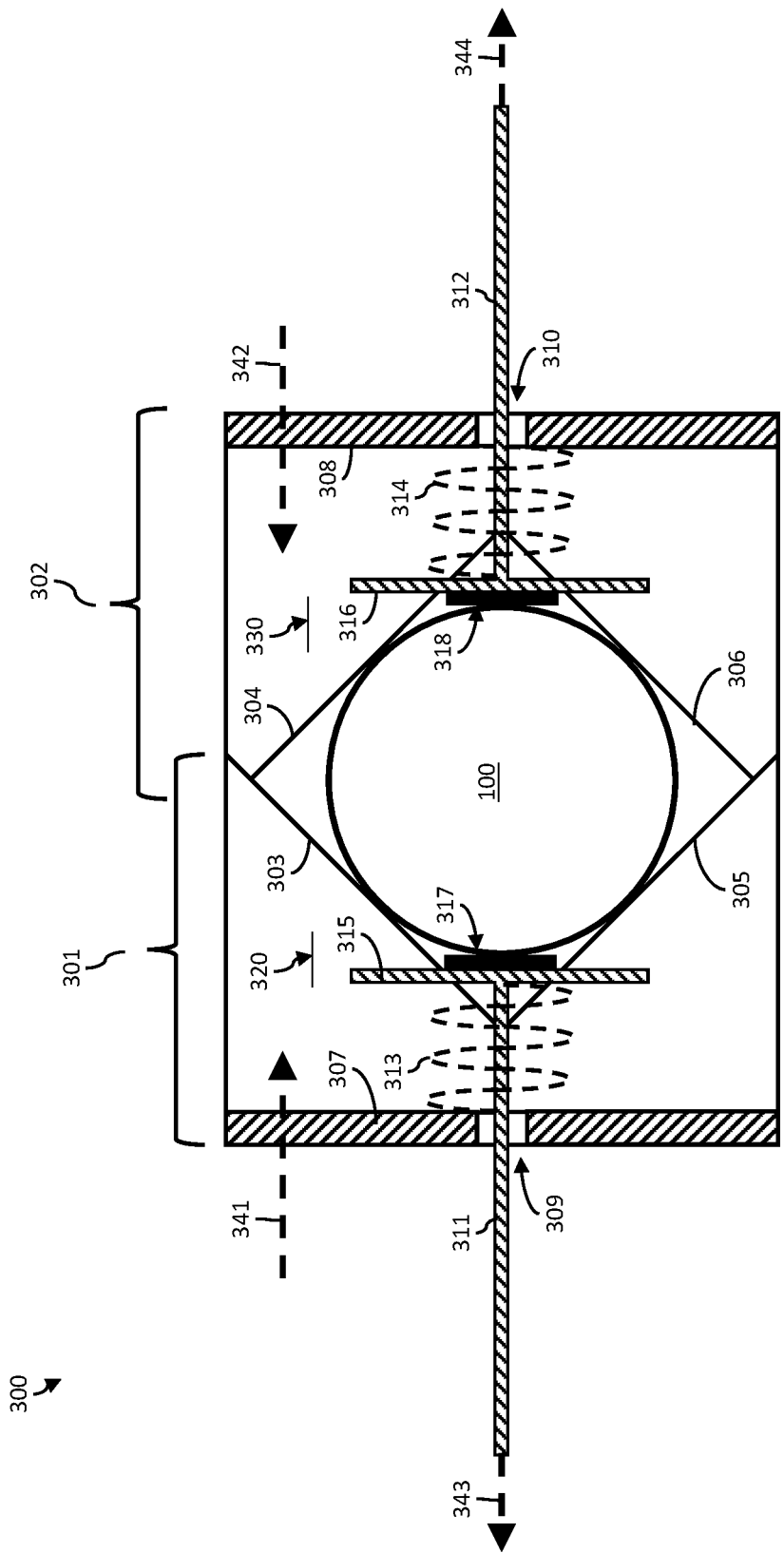
FIG. 3B is a top view of a possible implementation of the electrical measurement apparatus in a closed configuration according to possible implementations of the present disclosure.

FIG. 3B illustrates the electrical measurement of FIG. 3A in the closed configuration. The apparatus 300 further includes a first biasing mechanism 313 that is configured to maintain contact of the first electrode 317 with a first side of the plant stalk while the plant stalk is engaged with the first clamping portion 320 (i.e., the first ramp surface 303 and the second ramp surface 305 of the first clamping portion 320). The apparatus 300 may further include a second biasing mechanism 314 that is configured to maintain contact of the second electrode 318 with a second side of the plant stalk while the plant stalk is engaged with the second clamping portion 330 (i.e., the first ramp surface 304 and the second ramp surface 306 of second clamping portion 330).

The first biasing mechanism 313 may be implemented as a first spring positioned between the first plate portion 315 and the first base portion 307. The first rod portion 311 may be movable through and interior of the first spring. Moving the first plate portion 315 towards the first base portion 307 may move the first rod portion 311 in a first direction 343 through the opening 309 as the first the first spring is compressed. Likewise, the second biasing mechanism 314 may be implemented as a second spring positioned between the second plate portion 316 the second base portion 308. The second rod portion 312 may be movable through and interior of the second spring. Moving the second plate portion 316 towards the second base portion 308 may move the second rod portion 312 in a second direction 344 through the opening 310 as the first the second spring is compressed.

In the closed configuration, the V-shaped cantering feature of the first clamping portion 320 and the V-shaped centering feature of the second clamping portion 330 can hold the plant stalk 100 in alignment with the first electrode 317 and the second electrode 318 while the first biasing mechanism 313 and the second biasing mechanism 314 hold the first electrode 317 and the second electrode 318 against a surface of the plant stalk 100. These features of the apparatus 300, can reduce an offset between the plant stalk 100 and the electrodes. Additionally, these features of the apparatus 300 can reduce a gap between the pant stalk 100 and the first electrode 317 and/or the second electrode 318.

In some implementations, the first biasing mechanism 313 and the second biasing mechanism can be collectively referred to as biasing mechanisms. In some implementations, the biasing mechanisms may be different than the springs shown in FIG. 3A. For example, in some implementations, one or more of the biasing mechanisms can include a leaf spring, an elastomeric material, a screw mechanism, a wedge, mechanism, a lever mechanism, a cam mechanism, or a latch mechanism.

Figure 4:
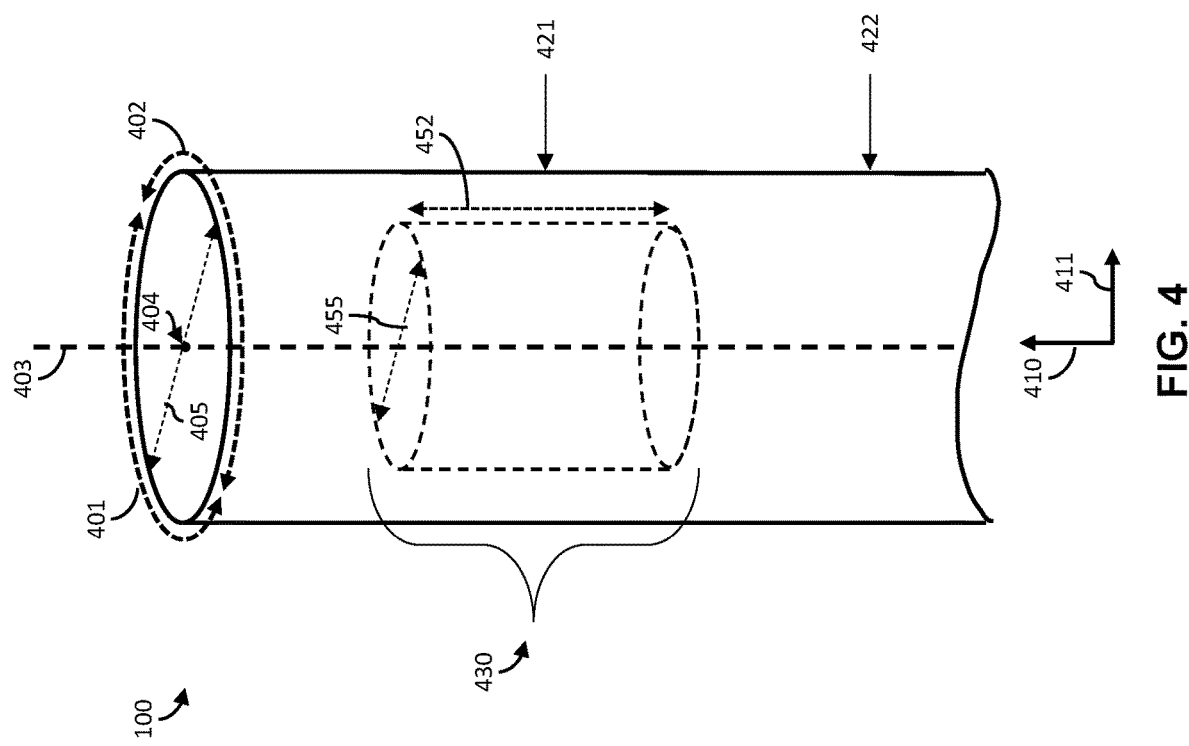
FIG. 4 is a perspective view of a plant stalk according to an implementation of the present disclosure.

FIG. 4 is a perspective view of a plant stalk according to an implementation of the present disclosure. The plant stalk 100 can have shape that approximates the cylindrical shape shown. Accordingly, in practice the terminology discussed below may be considered approximate to the ideal shape shown.

As shown in FIG. 4, the plant stalk 100 includes a longitudinal axis 403 at a center 404 of the plant stalk and directed along a longitudinal axis 410 of the plant stalk. Positions along the length of the plant stalk may be position located at different positions along the longitudinal axis 410 of the plant stalk. As shown, a first location 421 and a second location 422 are two possible locations along a length of the plant stalk.

A surface of the plant stalk may include a first side 401 and a second side 402 that can be defined as diametrically opposite sides of the plant stalk 100. For example, the first side 401 may include a first half of a circumference of the plant stalk and the second side may include a second half of the circumference of the plant stalk. A center of the first half and a center of the second half may define a stalk diameter 405 of the plant stalk. In a possible implementation, a first electrode may be positioned in contact with the first side 401, while a second electrode may be positioned in contact with the second side. In another possible implementation, the first electrode and the second electrode may be position in contact with the same side (i.e., the first side 401 or the second side 402).

The plant stalk may include a void 430. The void may include a void diameter 455 and a void length 452. The void diameter may be aligned with a transverse axis 411 of the plant stalk 100. A ratio of the void diameter 455 to the stalk diameter 405 may be correspond to an amount of damage of the plant stalk. For example, a ratio of zero may correspond to no damage. As shown in FIG. 4, the first location 421 may is a location that includes damage and therefor would have a ratio that is greater than zero, while the second location 422 is a location that includes no damage and therefore would have a ratio that is equal to zero.

Figure 5C:
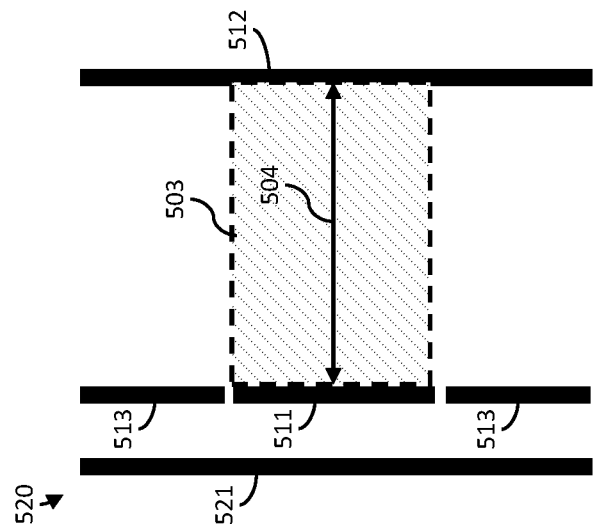
FIGS. 5A-5C are side views of electrode configurations for electrical measurements of a plant stalk according to possible implementations of the present disclosure.
Figure 5B:
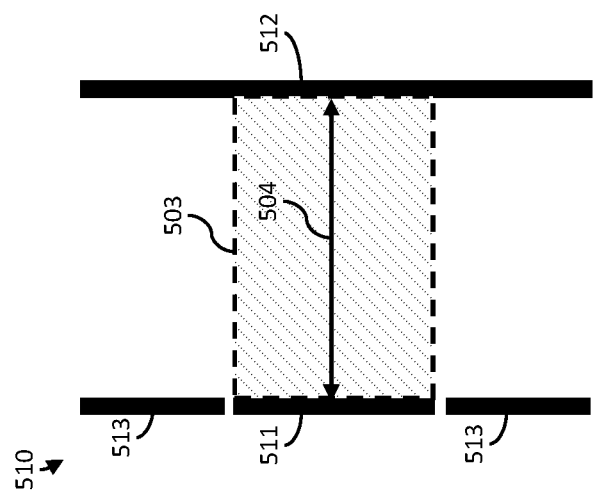
Figure 5A:
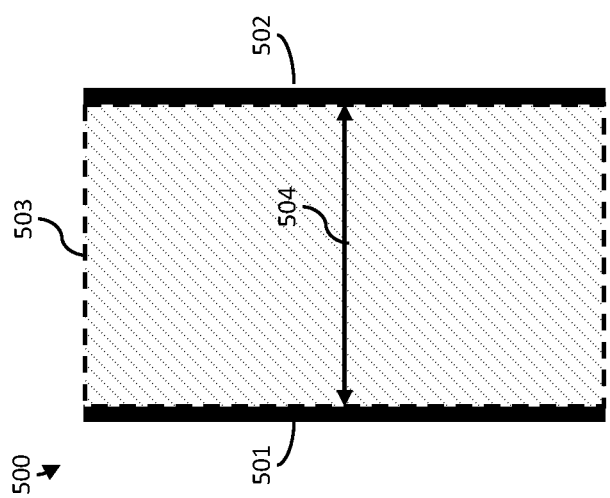

FIGS. 5A-5C are side views of electrode configurations for electrical measurements of a plant stalk according to possible implementations of the present disclosure. The electrodes may be any shape. For example, the electrodes may be circular. The electrodes can be any size. For example, the electrodes may be the same size. The electrodes may be aligned and spaced apart to form a capacitor having a capacitor gap 504. As discussed, the capacitor gap 504 may be approximately equal to the stalk diameter 405.

FIG. 5A is a first configuration 500 of a capacitor that can be used for the electrical measurement. The first configuration 500 includes a first electrode 501 and a second electrode 502 spaced apart by a capacitor gap 504. The first electrode 501 and the second electrode 502 may be sized the same to define a test area 503. The test area 503 corresponds can contain the electric fields of the capacitor and therefore a test area of a stalk may correspond to the test area 503 of the capacitor 500. The first configuration 500 capacitor may include fringe fields that can affect the precision and/or accuracy of the electrical measurement. Accordingly, the capacitor may be implemented using configurations to reduce these fringe fields.

FIG. 5B is a second configuration 510 of a capacitor that can be used for the electrical measurement. The second configuration 510 includes a guarded electrode 511 and a counter electrode 512. The guarded electrode 511 may be implemented as conductor having a circular (i.e., disk) shape. The second configuration 510 may further include a guard ring. The guard ring may be a conductor shaped into an annual ring that surrounds the guarded electrode so that a circular gap is formed between the guarded electrode 511 and the guard ring 513. The guard ring 513 may be electrically driven to so that the test area 503 includes homogeneous electric fields and is not significantly affect by fringe fields in areas of the guard ring.

FIG. 5C is a third configuration 520 of a capacitor that can be used for the electrical measurement. The third configuration 520 includes a guarded electrode 511 and a counter electrode 512. The guarded electrode 511 may be implemented as conductor having a circular (i.e., disk) shape. The second configuration 510 may further include a guard ring electrode. The guard ring may be a conductor shaped into an annual ring that surrounds the guarded electrode so that a circular gap is formed between the guarded electrode 511 and the guard ring 513. The guard ring 513 may be electrically driven to so that the test area 503 includes homogeneous electric fields and is not significantly affect by fringe fields in areas of the guard ring. The third configuration 520 further includes a guarded back 521 electrode that can further reduce fringe fields in the direction of the guarded back 521 electrode.

The configurations shown are provided as possible examples, and variations may exist provided that they can generate an electrical field to measure a defect (i.e., void) in the interior of the plant stalk. Some possible variations can include, a capacitor bank having multiple electrodes and a capacitor including coplanar capacitor electrodes.

Figure 6:
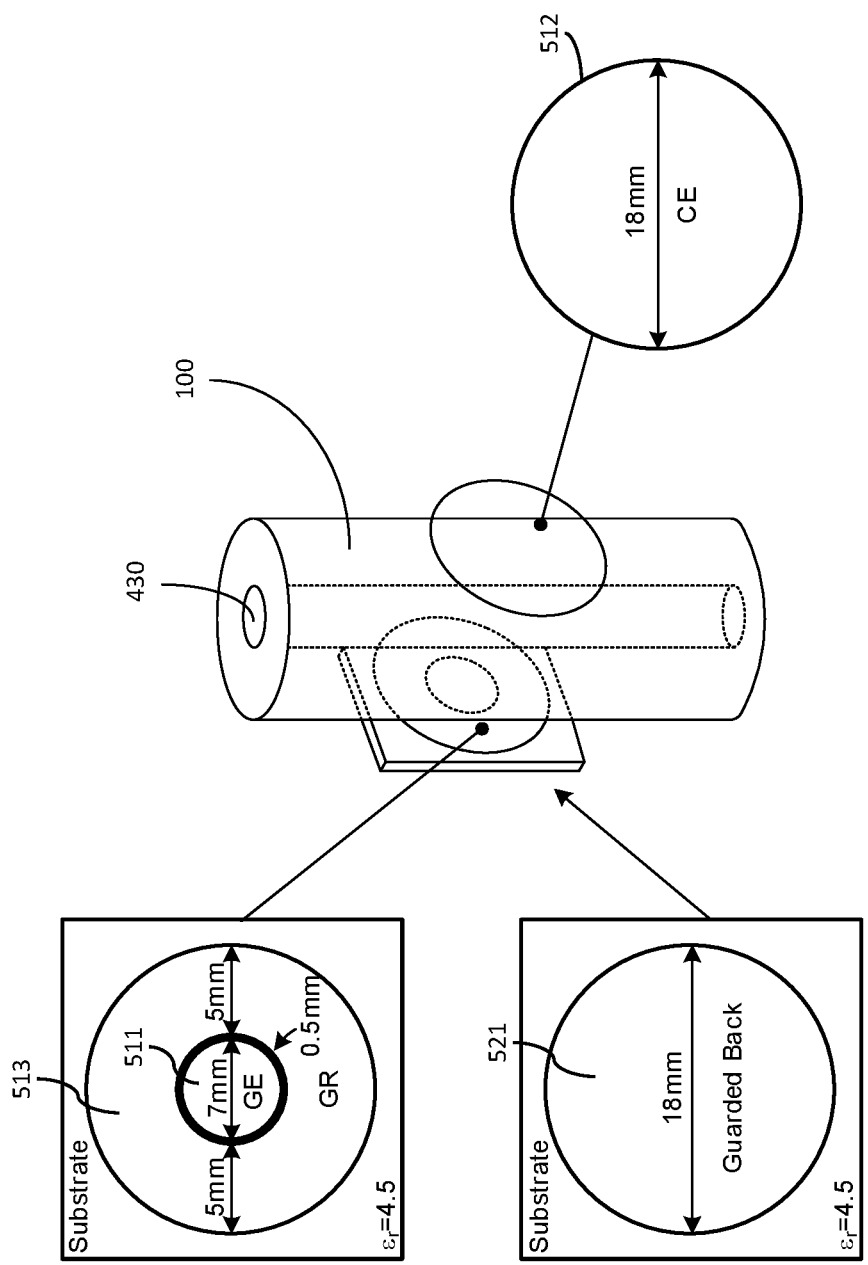
FIG. 6 illustrates an electrical measurement setup according to a possible implementation of the present disclosure.

FIG. 6 illustrates an electrical measurement setup according to a possible implementation of the present disclosure. As shown, the setup can include a counter electrode 512 (i.e., CE) is positioned on one side of a plant stalk 100. The counter electrode can be a circular conductor (e.g., copper) that is approximately 18 millimeters (mm) in diameter.

The setup can also include a guarded electrode 511 (i.e., GE) position on an opposite side of the plant stalk 100. The guarded electrode 511 can be a circular conductor that is approximately 7 mm is diameter. The setup can also include a guard ring (i.e., GR) electrode 513. The guard ring electrode 513 can be an annular ring having a thickness of approximately 5 mm and defining a gap between the guarded electrode and the guard ring of approximately 0.5 mm. The guarded electrode and the guard ring electrode can be conductors disposed on substrate having a relative permittivity of approximately 4.5.

The setup can also include a guarded back electrode 521 (i.e., GB), positioned behind the guarded electrode (GE) with respect to the plant stalk 100. For example, the guarded back electrode 521 can be a conductor disposed on an opposite side of the substrate including the guarded electrode 511.

The plant stalk 100 can include a void 430 resulting from damage. As mentioned, a ratio between a diameter of the void 430 and a diameter of the plant stalk can be sensed as an amount of damage to the plant stalk 100. The amount of damage may be sensed by the setup as a decrease in the capacitance between the guarded electrode 511 and the counter electrode 512. The capacitance can be affected by misalignments in the test setup.

Figure 7B:
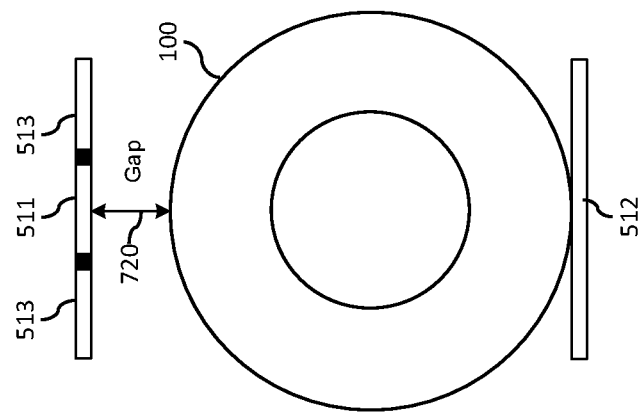
FIG. 7A-7B illustrate misalignments of electrodes and a plant stalk according to possible implementations of the present disclosure.
Figure 7A:
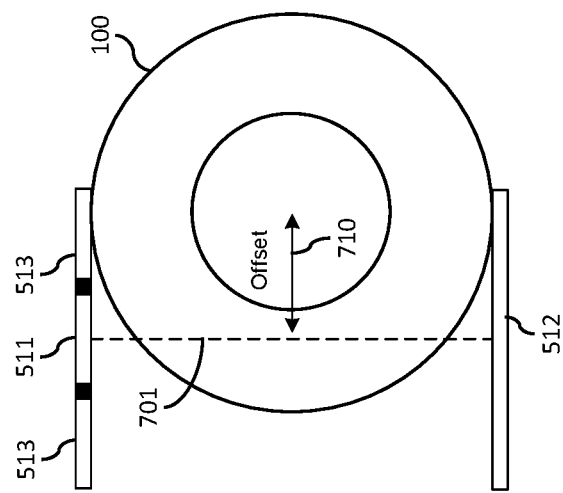

FIG. 7A-7B illustrate misalignments of electrodes and a plant stalk according to possible implementations of the present disclosure. A plant stalk may be considered aligned with the electrodes when a test area defined by the electrodes is substantially aligned with the center of the plant stalk and does not substantially include areas outside the plant stalk.

FIG. 7A illustrates an offset misalignment (i.e., offset) between the electrodes (i.e., test area) and the plant stalk 100. As shown, an offset 710 is a length between a center of the plant stalk and a centerline between a center of the guarded electrode 511 and a center of the center counter electrode 512.

FIG. 7B illustrates a gap misalignment (i.e., gap) between the electrodes (i.e., test area) and the plant stalk 100. As shown, a gap 720 is a length between a surface of the plant stalk 100 and the guarded electrode 511. Additionally, or alternatively, a gap 720 may be a length between the surface of the plant stalk 100 and the counter electrode 512. The offset misalignment and the gap misalignment can affect capacitance measurement results.

Figure 8C:
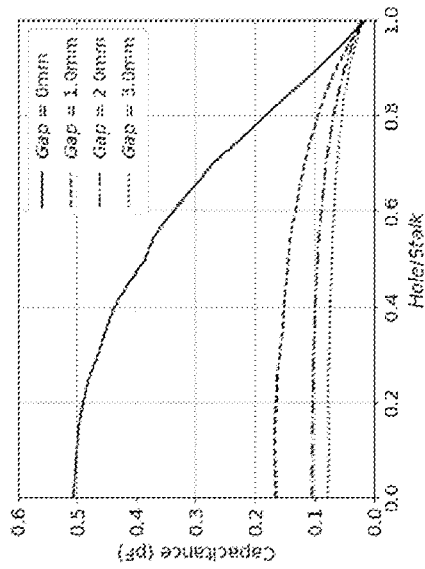
FIGS. 8A-8C illustrate the effects of misalignments of electrodes and a plant stalk on electrical measurements according to possible implementations of the present disclosure.
Figure 8B:
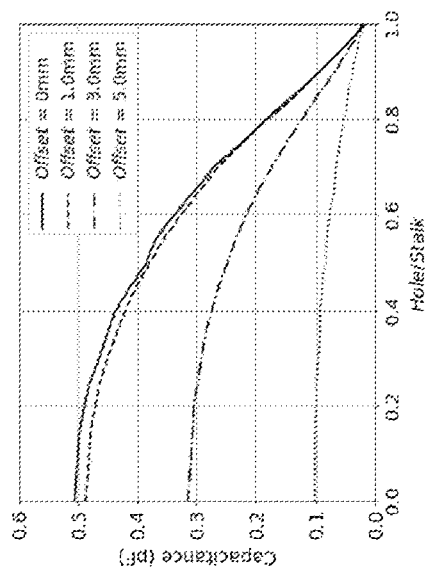
Figure 8A:
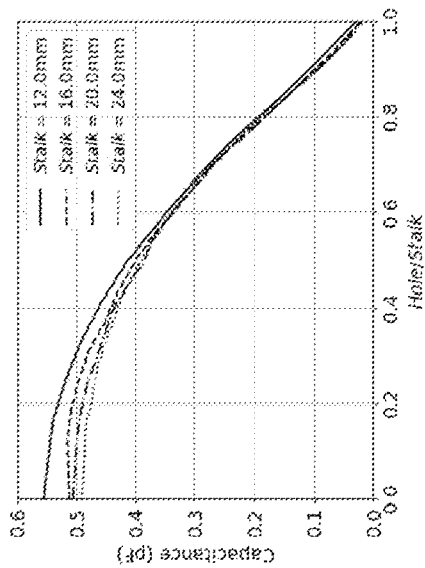

FIGS. 8A-8C illustrate the effects of misalignments of electrodes and a plant stalk on electrical measurements according to possible implementations of the present disclosure. FIGS. 8A-8C are capacitance measurements versus damage to the plant stalk, which is defined as the ratio between the diameter of the void (i.e., hole) in the plant stalk to the diameter of the plant stalk. Each graph includes measurements (i.e., traces) from different diameter plant stalks.

FIG. 8A is a graph illustrating the capacitance versus damage for a test setup in which the offset and the gap misalignments are zero. The graph shows a decrease in capacitance as the amount of damage increases. The graph further shows that without an offset or a gap, that the measurements are relatively independent of the different plant stalk diameters.

FIG. 8B is a graph illustrating the capacitance versus damage for a test setup for increasing offsets. The graph shows the general decrease in capacitance as the amount of damage increases. The graph also shows that the measured capacitance for a particular amount of damage decreases at the offset is increased. Accordingly, determining an amount of damage or determining that damage is present may be affected by an offset. For example, damage may be detected when no damage exists when an offset is present in the test setup.

FIG. 8C is a graph illustrating the capacitance versus damage for a test setup for increasing gaps. The graph shows the general decrease in capacitance as the amount of damage increases. The graph also shows that the measured capacitance for a particular amount of damage decreases at the gap is increased. Accordingly, determining an amount of damage or determining that damage is present may be affected by a gap. For example, damage may be detected when no damage exists when a gap is present in the test setup. The apparatus of the present disclosure can reduce (e.g., make zero) misalignments (e.g., gap and/or offset) to increase a precision of the electrical measurement.

Figure 9:
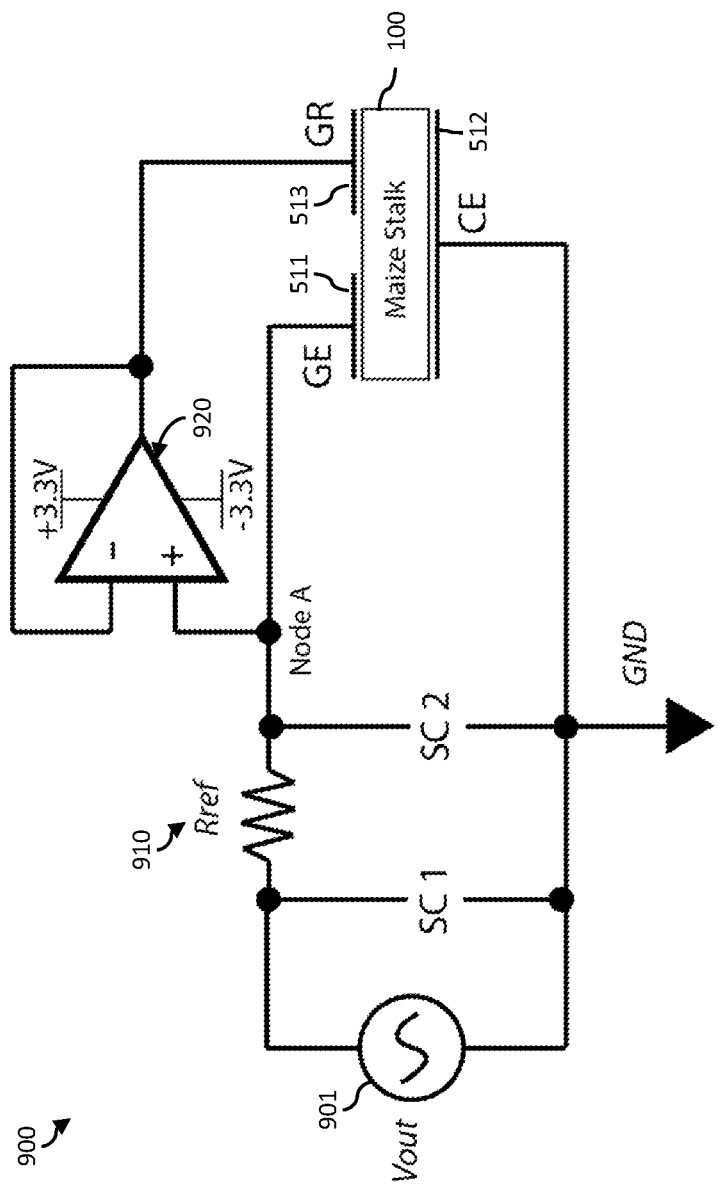
FIG. 9 is a schematic of a circuit for an electrical measurement of a plant stalk according to a first possible implementation of the present disclosure.

FIG. 9 is a schematic of a circuit for an electrical measurement of a plant stalk according to a first possible implementation of the present disclosure. The circuit 900 includes a voltage source 901 connected between a reference resistor ($R_{REF}$) and a ground (GND). The voltage source 901 can generate a test signal that is an alternating current (AC) voltage (e.g., 1V peak-to-peak) having a frequency (F) that can be swept through a range of frequencies (e.g., 500 Hz≤F≤100 KHz). The test signal can be coupled to the reference resistor 910 having a high resistance (e.g., 1 MΩ). The reference resistor 910 is coupled in series with the capacitor that includes the plant stalk 100. For example, the reference resistor 910 can be coupled to a guarded electrode 511 (GE) of the capacitor, and a counter electrode 512 (CE) of the capacitor can be coupled o a ground of the circuit 900. The circuit 900 may further includes an amplifier 920 (i.e., buffer amplifier) having unity gain coupled between the reference resistor ($R_{REF}$) and the guard ring electrode 513 (GR).

In a test cycle, a first voltage (SC1) and a second voltage (SC2) may be measured and compared to determine a voltage amplitude and phase across the reference resistor ($R_{REF}$) as the voltage source 901 is swept through the range of frequencies. From these measurements, a capacitance of between the guarded electrode (GE) and the counter electrode (CE) may be determined. From this capacitance a damage to the plant stalk 100 may be detected and/or quantified.

Figure 10:
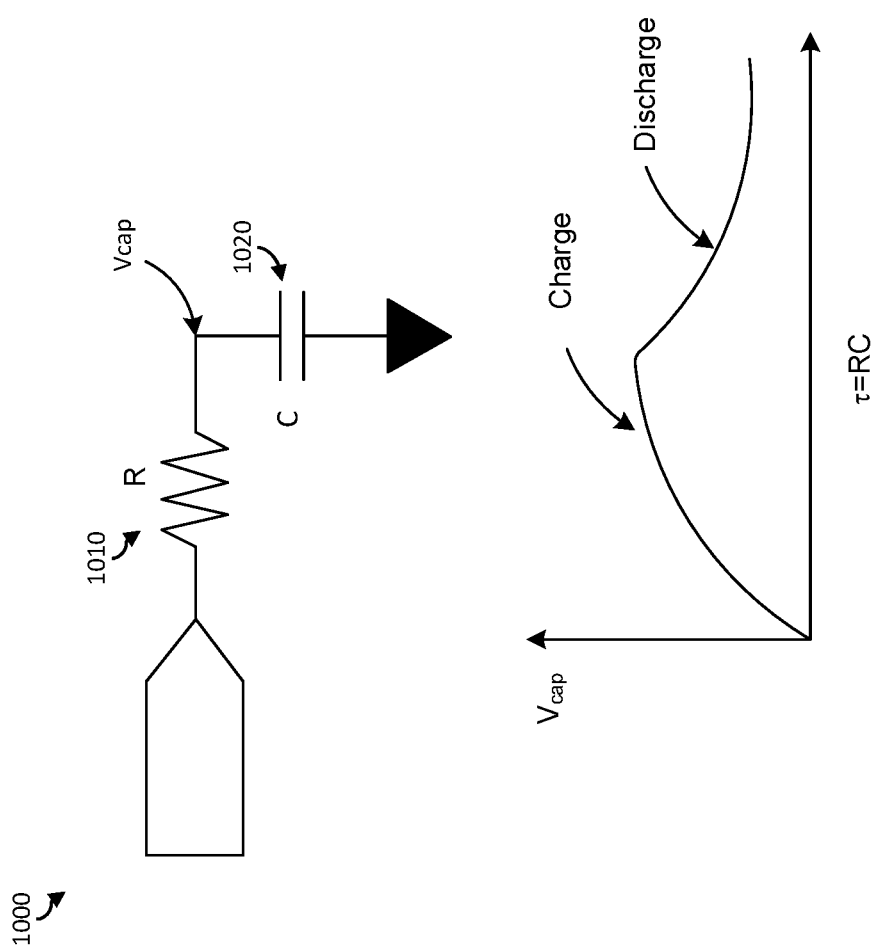
FIG. 10 is a schematic of a circuit for an electrical measurement of a plant stalk according to a second possible implementation of the present disclosure.

FIG. 10 is a schematic of a circuit for an electrical measurement of a plant stalk according to a second possible implementation of the present disclosure. The circuit 1000 includes a reference resistor 1010 that is in series with the plant stalk capacitance 1020. A digital source may generate a test signal that is coupled to the RC circuit formed by the reference resistor 1010 and the plant stalk capacitance 1020. A first transition of the digital source from a LOW level (e.g., zero volts) to a HIGH level (e.g., 3.3 volts) can create a corresponding voltage at a node between the reference resistor 1010 and the plant stalk capacitance 1020 that increases according to an RC time constant. A second transition of the digital source from the HIGH level to the LOW level can create a corresponding voltage at a node between the reference resistor 1010 and the plant stalk capacitance 1020 that decreases according to the RC time constant. The plant stalk capacitance may be determine based on the RC time computed from voltage increase and/or the voltage decrease resulting from the test signal.

Figure 11:
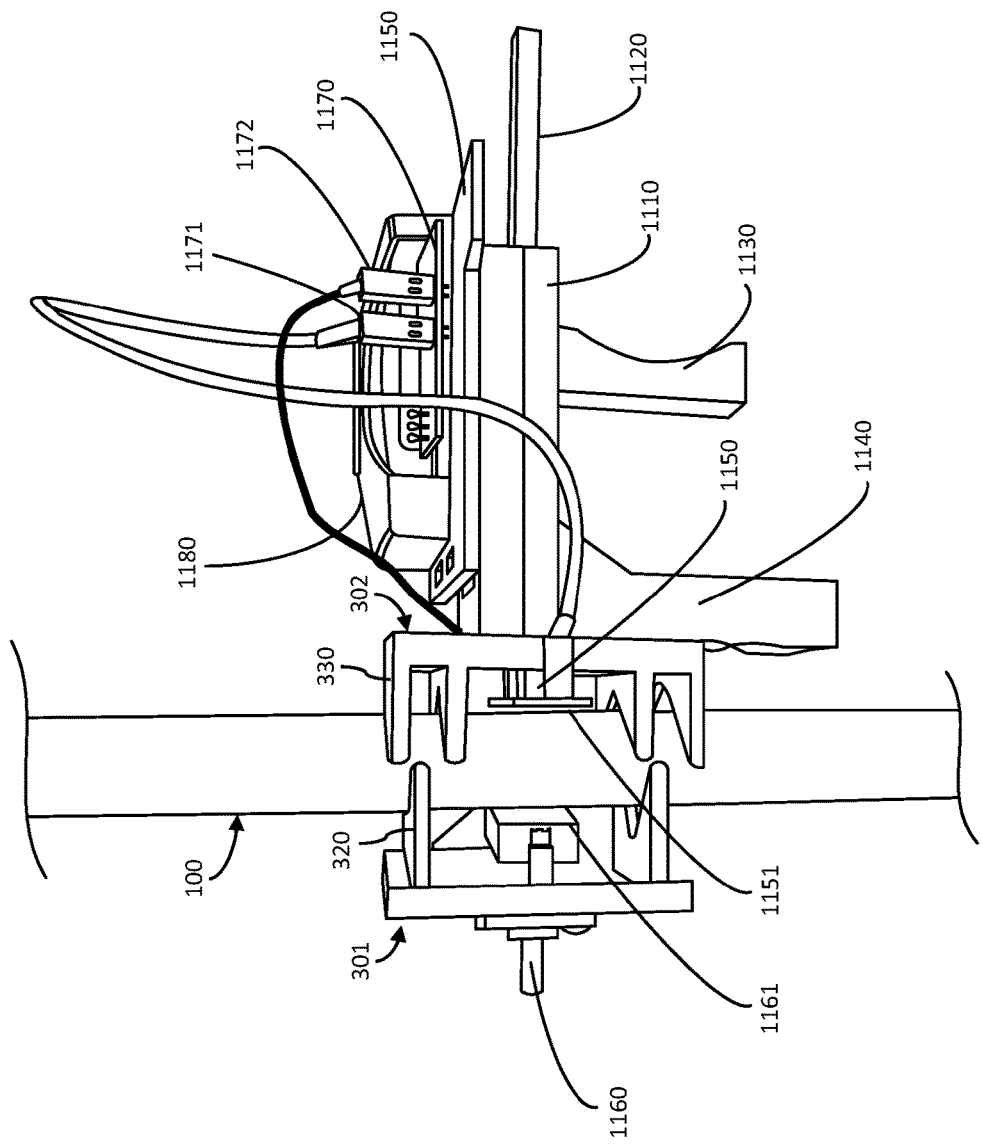
FIG. 11 is a side view of the apparatus for an electrical measurement of a plant stalk according to an implementation of the present disclosure.

FIG. 11 is a side view of the apparatus for an electrical measurement of a plant stalk according to an implementation of the present disclosure. The apparatus to measure an impedance (e.g., capacitance) of a plant stalk 100 (e.g., maize stalk) can include a first arm 301 (i.e., first electrode guide) positioned on a first side of the plant stalk 100 and a second arm 302 (i.e., second electrode guide) positioned on a second side of the plant stalk 100. Either arm, or both arms, may be movable towards the plant stalk by a clamping force. Either arm, or both arms, may be fixed.

The clamping force may be generated by a spring. Accordingly, the apparatus may include a spring mechanism that is housed in a spring body 1110. The spring mechanism can pull the first arm 320 towards the second arm 330. The first arm 301 may be coupled to a plunger 1120. An opening force (i.e., decoupling force) that is greater than the clamping force may be exerted on the plunger to push the first arm 301 away from the second arm.

The apparatus may further include a trigger 1130 and a handle 1140. A user may hold the apparatus by the handle and grip the trigger. The trigger 1130 may be coupled to the plunger 1120 and the opening force may be generated by a user when the user pulls the trigger 1130 towards the handle 1140. In other words, the trigger can be configured to actuate the spring-loaded plunger to open and/or close a space between the arms (i.e., electrode guides). When the trigger is released, the arms close and clamp onto the plant stalk and center the electrodes (e.g., GE, CE) in the process. The electrodes are pressed against the plant stalk with small springs to ensure good contact with the plant stalk.

The first arm 301 includes a first clamping portion 320 and the second arm 302 includes a second clamping portion 330. As shown, additional clamping portions may be included. For example, the first arm 301 includes an upper and a lower clamping portion, while the second arm 302 includes an upper and lower clamping portion for the upper clamping portion of the first arm 301 and an upper and lower clamping portion for the lower clamping portion of the first arm. In total, the apparatus shown includes 6 clamping portions that interleave when the apparatus is clamped on the stalk. In other implementations, the arms may include different number of clamping portions arranged in different configurations than shown.

The apparatus further includes a guarded electrode (GE) and guard ring (GR) circuit 1151 that is coupled to a GE probe 1150 (i.e., GE holder). The apparatus further includes a counter electrode circuit 1161 that is coupled to a CE probe 1160 (i.e., CE holder). The GE is coupled to an interface circuit 1170 by a guarded cable 1171. The CE is coupled to the interface circuit 1170 by a ground cable 1172. The interface circuit 1170 is coupled to a test measurement computer (e.g., DIGILENT™).

FIG. 12 is a flowchart of a method for detecting damage to a plant stalk according to an implementation of the present disclosure. The method 1200 includes coupling 1210 (e.g., clamping) a centering mechanism and a probe to a plant stalk at a location (e.g., first location). The method 1200 further includes applying 1220 a test signal to an electrode (e.g., guarded electrode). The method 1200 further includes sensing 1230 a response (e.g., voltage amplitude, voltage phase) corresponding to the electrode. For example, the response of the electrode to the test signal may be measured at the electrode. The method 1200 further includes determining 1240 a capacitance of the plant stalk at the location based on the response. The method 1200 may further include detecting 1250 damage to the plant stalk based on the capacitance.

In the specification and/or figures, typical embodiments have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Some implementations may be implemented using various semiconductor processing and/or packaging techniques. Some implementations may be implemented using various types of semiconductor processing techniques associated with semiconductor substrates including, but not limited to, for example, Silicon (Si), Gallium Arsenide (GaAs), Gallium Nitride (GaN), Silicon Carbide (SiC) and/or so forth.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

It will be understood that, in the foregoing description, when an element is referred to as being on, connected to, electrically connected to, coupled to, or electrically coupled to another element, it may be directly on, connected or coupled to the other element, or one or more intervening elements may be present. In contrast, when an element is referred to as being directly on, directly connected to or directly coupled to another element, there are no intervening elements present. Although the terms directly on, directly connected to, or directly coupled to may not be used throughout the detailed description, elements that are shown as being directly on, directly connected or directly coupled can be referred to as such. The claims of the application, if any, may be amended to recite exemplary relationships described in the specification or shown in the figures.

As used in this specification, a singular form may, unless definitely indicating a particular case in terms of the context, include a plural form. Spatially relative terms (e.g., over, above, upper, under, beneath, below, lower, and so forth) are intended to encompass different orientations of the device in use or operation in addition to the orientation depicted in the figures. In some implementations, the relative terms above and below can, respectively, include vertically above and vertically below. In some implementations, the term adjacent can include laterally adjacent to or horizontally adjacent to.

The invention claimed is:

1. An apparatus, comprising:
   a centering mechanism configured to be coupled to a plant stalk;
   a probe movably coupled to the centering mechanism and having an electrode; and
   a first biasing mechanism configured to maintain contact of the electrode with a portion of the plant stalk while the centering mechanism is coupled to the plant stalk and during a measurement cycle using the electrode.

2. The apparatus according to claim 1, wherein the centering mechanism includes:

a first arm including a first centering feature configured to receive the plant stalk;
a second arm including a second centering feature to receive the plant stalk; and
a clamping mechanism configured to press the plant stalk between the first arm and the second arm so that the plant stalk is held by the first centering feature and the second centering feature.

3. The apparatus according to claim 2, wherein the first centering feature and the second centering feature reduce an offset between the plant stalk and the electrode when the plant stalk is held by the first centering feature and the second centering feature.

4. The apparatus according to claim 2, wherein:
the first centering feature is a first V-shape having a first opening facing a surface of the plant stalk; and
the second centering feature is a second V-shape having a second opening facing the surface of the plant stalk.

5. The apparatus according to claim 2, wherein:
the first arm is fixed with respect to the second arm; and
the second arm is movable with respect to the first arm.

6. The apparatus according to claim 1, wherein the electrode is a guarded electrode, and the probe further includes a counter electrode, the guarded electrode and the counter electrode.

7. The apparatus according to claim 6, wherein the guarded electrode and the counter electrode are configured to contact opposite sides of the plant stalk, respectively, during the measurement cycle.

8. The apparatus according to claim 6, wherein the guarded electrode and the counter electrode each contact a side of the plant stalk during the measurement cycle.

9. The apparatus according to claim 6, wherein the probe further includes a guard ring, the guard ring surrounding the guarded electrode in a plane of the guarded electrode.

10. The apparatus according to claim 1, wherein the probe includes a plunger having a rod portion movable in an opening of the centering mechanism and a plate portion configured to support the electrode.

11. The apparatus according to claim 10, wherein the first biasing mechanism is a spring positioned along the rod portion and configured to press the electrode on the plate portion against the portion of the plant stalk.

12. An apparatus for detecting damage to a plant stalk, comprising:
a centering mechanism and a probe coupled to the plant stalk at a location, the probe movably coupled to the centering mechanism via a biasing mechanism and having an electrode such that the biasing mechanism maintains contact of the electrode with the plant stalk; and
a circuit configure to:
apply a test signal to the electrode;
sense a response, at the electrode, to the test signal; and
output a capacitance of the plant stalk at the location based on the response.

13. The apparatus for detecting damage to the plant stalk according to claim 12, wherein:
the probe is a first probe, the biasing mechanism is a first biasing mechanism, the electrode is a first electrode, the apparatus including:
a first arm of the centering mechanism coupled to a first side of the plant stalk, the first arm also coupled to the first probe via the first biasing mechanism; and
a second arm of the centering mechanism coupled to a second side of the plant stalk, the second arm also coupled to a second probe via a second biasing mechanism, the second probe including a second electrode.

14. The apparatus for detecting damage to a plant stalk according to claim 13, wherein:
the first arm and the second arm are configurable in an open configuration in which the plant stalk can be positioned between the first arm and the second arm; and
the first arm and the second arm are configurable in a closed configuration to align the plant stalk and reduce an offset between the plant stalk and the first electrode and the second electrode, wherein in the closed configuration the first biasing mechanism presses the first electrode against a surface of the plant stalk and the second biasing mechanism presses the second electrode against the surface of the plant stalk to reduce a gap between the plant stalk and the first electrode and the second electrode.

15. The apparatus for detecting damage to the plant stalk according to claim 14, wherein
the capacitance is between the first electrode and the second electrode.

16. The apparatus for detecting damage to the plant stalk according to claim 12, wherein the test signal is an alternating current (AC) voltage that is swept through a range of frequencies.

17. The apparatus for detecting damage to the plant stalk according to claim 16, wherein the capacitance is an amplitude and phase of a voltage across a reference resistor that is coupled in series with the electrode.

18. The apparatus for detecting damage to the plant stalk according to claim 12, wherein the test signal is digital signal that is transition from a LOW level to a HIGH level.

19. The apparatus for detecting damage to the plant stalk according to claim 18, wherein the capacitance is based on an RC time constant of a voltage across a reference resistor that is coupled in series with the electrode.

* * * * *